United States Patent [19]

Schmidt et al.

[11] Patent Number: 5,314,827
[45] Date of Patent: May 24, 1994

[54] ISOTOPIC COMPOSITION ANALYZER

[75] Inventors: Hanns-Ludwig Schmidt, Landshut; Ramiro Medina, Marzling, both of Fed. Rep. of Germany

[73] Assignee: Fisons plc, Ipswich, England

[21] Appl. No.: 584,179

[22] Filed: Sep. 18, 1990

[30] Foreign Application Priority Data

Sep. 20, 1989 [GB] United Kingdom ................ 8921285

[51] Int. Cl.$^5$ ............................................. B01D 59/44
[52] U.S. Cl. .................................. 436/106; 436/127; 436/136; 436/145; 436/159; 436/161; 436/173; 250/282
[58] Field of Search ............... 436/106, 127, 136, 144, 436/145, 159, 161, 173; 73/23.37; 250/282

[56] References Cited

U.S. PATENT DOCUMENTS 3,066,220 11/1962 Nief et al. ......................... 250/41.9
4,916,313 4/1990 Hall et al. ........................... 250/282

FOREIGN PATENT DOCUMENTS 0306332 8/1989 European Pat. Off. ...... G01N 30/84

OTHER PUBLICATIONS

Hayes–31st An. Conf. Mass Spec. & Allied Topics, Boston, Mass. May, 1983, pp. 450–453.
Matthews, Hayes–Analytical Chemistry, vol. 50 (11) Sep. 1978, pp. 1465–1473.
Barrie, Bricout, Koziet–Biomedical Mass Spectrom, vol. 11 (11), 1984, pp. 583–588.
Preston, Owens–Analyst, Aug. 1983 vol. 108, pp. 971–977.
Santrock, Hayes–Anal. Chem. vol. 59 (1987) pp. 119–127.
DeNiro, Epstein–Anal. Chem. (1989), vol. 61, pp. 1887–1889.
Loginov, Kuznetsova, Semenov–Agrokhimiya, 1973, vol. 7, pp. 134–138. (English Abstract attached).
Steinmuller–Int. Lab., Jun., 1988, pp. 44–51.
Schneider, Frohne, Bruddereck–J. Chromatogr., 1982, vol. 245, pp. 71–83.
Kaiser, Rieder–Proc. Fourth Int. Clean Air Congress, Tokyo, 1977, pp. 451–454.
Sofer–Anal. Chem. (1986), vol. 58, No. 9, pp. 2029–2032.

Primary Examiner—James C. Housel
Assistant Examiner—David Redding
Attorney, Agent, or Firm—Chilton, Alix & Van Kirk

[57] ABSTRACT

An on-line mass spectrometric method and apparatus for the determination of the isotopic composition of at least oxygen, hydrogen and nitrogen in a compound or mixture of compounds. A mixture contained in syringe 6 is injected through injector 7 on a chromatographic column 1. Compounds eluting from the column 1 pass into a catalytic reactor 14 containing carbon and are decomposed to produce carbon monoxide, molecular nitrogen, and molecular hydrogen. These gases are analyzed by an isotope-ratio mass spectrometer 4 so that the isotopic composition of the oxygen, nitrogen and hydrogen comprised in the original compound can be determined. A second chromatographic column 24 may be provided to separate carbon monoxide and nitrogen before they are passed into the spectrometer 4, thereby allowing a low resolution spectrometer to be used for the analysis of both gases at m/e 28 daltons.

9 Claims, 3 Drawing Sheets

ISOTOPIC COMPOSITION ANALYZER

This invention relates to a method of determining the quantitative isotopic composition of certain elements comprised in a compound, and to apparatus for carrying out the method.

A preferred method of determining the isotopic composition of the elements comprised in an organic compound is to completely convert the compound into analysis gases, e.g. carbon dioxide, nitrogen, etc., which may then be mass spectrometrically analyzed to determine the isotopic composition of the elements in the original compound Usually, the conversion to analysis gases is carried out manually and is extremely laborious. However, on-line methods are known for some elements, for example carbon.

The determination of carbon isotopic ratios presents the least difficulty. Hayes (31st Ann.Confr. on Mass Spectrometry and Allied Topics, Boston, Mass., May, 1983, pp 450-453) describes a method in which the sample is pyrolyzed with excess oxygen in the presence of cupric oxide and silver to yield carbon dioxide and nitrogen, which can be used as analysis gases to determine the isotopic composition of the carbon and nitrogen in the original sample. The process can be carried out both off-line and on-line. In the former method, the gas is collected in reservoirs, the contents of which are subsequently analyzed on a conventional isotope-ratio mass spectrometer. A convenient on-line method involves the conversion of a conventional carbon elemental analyzer. Such an analyzer produces a flow of carbon dioxide which can be directly introduced into the mass spectrometer. Similarly, a nitrogen elemental analyzer, or the nitrogen channel of a multi-element analyzer, can be used to feed nitrogen directly into the mass spectrometer. An on-line pyrolysis system for the conversion of an organic compound eluting from a gas-chromatographic column to carbon dioxide and its subsequent introduction into a mass spectrometer has been described by Matthews and Hayes in Analytical Chemistry, 1978, vol 50 (11), pp 1465, and improved versions of this process are described by Barrie, Bricout and Koziet, (Biomedical Mass Spectrom. 1984, vol 11(11), pp 583 and in European Patent Application publication number 306332. A system for nitrogen determination has been described by Preston and Owens (Analyst, 1983, vol 108, pp 971-977).

The determination of the isotopic composition of the oxygen and hydrogen in an organic sample is more difficult. Santrock and Hayes (Anal. Chem. 1987, vol 59, pp 119-127) report the adaption of the Unterzaucher procedure for the elemental analysis of oxygen for isotopic analysis. The procedure involves the steps of pyrolyzing the sample, conversion of the oxygenated pyrolysis products to carbon monoxide by equilibration with carbon at high temperature, and finally the oxidation of the carbon monoxide to carbon dioxide by means of iodine pentoxide. Santrock and Hayes report that great care and elaborate calibration and correction procedures were necessary for accurate results, even using off-line collection of the carbon dioxide, and the process has not been adapted for on-line analysis. An alternative procedure described by Hayes (ibid) involves the pyrolysis of the sample in a sealed nickel tube, but this process is not amenable to on-line use. Another similar method, also unsuitable for on-line use, has been described by DeNiro and Epstein (Anal.Chem, 1989, vol.61, pp 1887-9). Another process, involving the pyrolysis of the sample in vacuum at 1150° C. and the subsequent chromatographic trapping of the CO produced has been described by Loginov, Kuznetsova and Semenov (Agrokhimiya, 1973, vol.7, pp 134-8) but does not appear to have been adapted for on-line use, nor indeed verified by other workers.

The determination of hydrogen is also less satisfactory than that of carbon. One prior method is to collect the water produced by the oxygen-rich pyrolysis and subsequently reduce it to hydrogen using heated zinc or uranium, and this process has been adapted for on-line use. However, the complete recovery of the water is very difficult to achieve and the results obtained using the technique are not particularly accurate.

A need therefore exists for an improved method for determining on-line the isotopic composition of certain elements comprised in a sample, especially hydrogen and oxygen, and it is an object of the present invention to provide such a method. Other objects of the present invention are to provide apparatus for carrying out that method, and to provide a method of determining the isotopic composition of elements comprised in at least some of the components of a mixture without the need to prepare samples of the pure components.

In accordance with these objectives the invention provides a method of determining the isotopic composition of at least one element selected from oxygen, nitrogen and hydrogen in a sample, said method comprising the sequential operation of the following steps:

1) causing a carrier gas which does not comprise said selected element to flow through a heated catalytic reactor said reactor containing elemental carbon;
2) introducing said sample into said flow of carrier gas before it enters said catalytic reactor so that said sample is pyrolyzed in said reactor, and:
   a) any carbon present in said sample is converted to elemental carbon which is deposited in said reactor;
   b) any oxygen present in said sample is substantially completely converted to carbon monoxide by reaction with elemental carbon in said reactor;
   c) any hydrogen present in said sample is substantially completely converted to molecular hydrogen; and
   d) any nitrogen present in said sample is substantially completely converted to molecular nitrogen;
3) conveying at least some of the gases emerging from said catalytic reactor into a mass spectrometer; and
4) determining the isotopic composition of at least one said element selected from the group consisting of oxygen, nitrogen and hydrogen by mass spectrometric measurements made on said carbon monoxide, molecular nitrogen or molecular hydrogen, respectively.

As discussed below, it is necessary for elemental carbon to be present in excess in the reactor for the catalytic conversion to take place. The carbon may be deposited in the reactor prior to the admission of a sample by placing carbon in the reactor or by pyrolyzing a carbonaceous compound in the reactor whereby a deposit of carbon will be formed. In certain circumstances, sufficient carbon may be deposited in the reactor by the pyrolysis of the sample being analyzed, but this is a less preferred method.

The reaction upon which the invention is based may be illustrated by the reaction scheme:

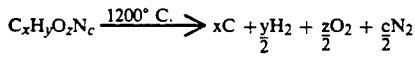

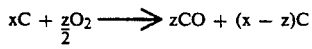

A suitable catalyst for this process may comprise the carbon itself. In this case, the reactor should be maintained at about 1000° C. If hydrogen is not to be determined, the catalyst may comprise a platinum/rhodium alloy maintained at 1200° C. The latter catalyst has been used with considerable success in oxygen-selective flame ionization detectors (OSD's) for gas chromatography (see, for example, Steinmüller, Int. Lab. June, 1988, pp 44–51, Schneider, Frohnë and Bruderreck, J, Chromatogr. 1982, vol 245, pp 71–83,). These OSD's incorporate a further reactor for converting the carbon monoxide to methane which is easily detected on a conventional flame ionization detector. This methanization step can also be used in certain methods according to the invention (see below). It will be appreciated that it has not previously been recognized that these reactions would be useful for quantitative isotopic ratio mass spectrometry.

The invention further provides a method of determining the isotopic composition of at least one element selected from oxygen, nitrogen and hydrogen in a carbonaceous sample, said method comprising the sequential operation of the following steps:

1) introducing a said carbonaceous sample into a flow of carrier gas which does not comprise said selected element;
2) conveying said carrier gas and said carbonaceous sample into a heated catalytic reactor, wherein:
   a) said carbonaceous sample is pyrolyzed within said reactor to produce elemental carbon which is deposited in said reactor;
   b) any oxygen present in said carbonaceous sample is substantially completely converted to carbon monoxide by reaction with elemental carbon present in said reactor;
   c) any hydrogen present in said carbonaceous sample is substantially completely converted to molecular hydrogen; and
   d) any nitrogen present in said carbonaceous sample is substantially completely converted to molecular nitrogen;
3) conveying at least some of the gases emerging from said catalytic reactor into a mass spectrometer, and
4) determining the isotopic composition of at least one said element selected from the group consisting of oxygen, nitrogen and hydrogen by mass spectrometric measurements made on said carbon monoxide, molecular nitrogen or molecular hydrogen, respectively.

It will be appreciated that if the reactor contains an excess of carbon the method of the invention may be used for the determination of oxygen in a non-carbonaceous compound. In particular, the invention provides a convenient and accurate method for the determination of the isotopic composition of oxygen and hydrogen in water.

The invention also comprises a method of determining the the isotopic composition of carbon comprised in a sample, said method comprising the steps of:

1) introducing said sample into a flow of non-carbonaceous carrier gas and conveying said carrier gas to a catalytic reactor, said reactor containing elemental carbon, wherein said sample is pyrolyzed to deposit elemental carbon in said reactor;
2) introducing into said catalytic reactor a non-carbonaceous oxygenated compound which reacts with said elemental carbon to produce carbon monoxide,
3) conveying at least some of the gases emerging from said catalytic reactor into a mass spectrometer; and
4) determining the isotopic composition of the carbon comprised in said sample by mass spectrometric measurements made on said carbon monoxide.

For carbon isotope ratio measurements, the reactor must not contain carbon deposited from a previous sample, and the oxygenated compound, which must not contain carbon, is preferably water.

The invention further provides a method of determining the isotopic composition of the elements comprised in the individual constituents of a mixture. A sample of the mixture is injected into a carrier gas which then flows through a gas chromatographic column before entering the catalytic reactor. In this way the mixture may be separated into its constituents which elute sequentially so that the isotopic composition of each can be determined in turn. The chromatographic column and conditions are selected to provide good resolution of the constituents whose isotopic compositions are to be determined.

The chromatographic system employed preferably incorporates facilities for allowing only selected constituents to enter the catalytic reactor. This is especially useful when it is necessary to determine the isotopic composition of only a few constituents of a complex mixture.

Further preferably, a system similar to that disclosed in European Patent Application publication number 306332 may be employed. This system provides a chromatographic arrangement which maintains a constant flow of carrier gas into the mass spectrometer under all circumstances. It further provides a method of introducing one or more reference gases into the mass spectrometer at times when no component of interest is eluting from the column, thereby increasing the accuracy of the isotope ratio measurements.

In the case of a sample comprising both nitrogen and oxygen, it is clear that unless a high resolution mass spectrometer is employed the isotopic analysis of the carbon monoxide and nitrogen produced in the catalytic reactor will be difficult because both have a nominal mass of 28 daltons. Two methods are envisaged for handling this situation.

The first preferred method comprises selectively absorbing at least one of the constituents of the effluent from the catalytic reactor prior to its introduction into the mass spectrometer. In this way the carbon monoxide may be separated from the nitrogen, conveniently by passing the reactor effluent through a chromatographic column, so that the two gases can be sequentially analyzed by the mass spectrometer. The chromatographic column may comprise a "Poraplot Q" or molecular sieve column maintained at −4° C. Alternatively, the selective absorption may be achieved by trapping the carbon monoxide. This embodiment is appropriate only in cases where oxygen isotopic ratios are not required. Trapping may be achieved by a cooled molecular sieve or a chemical material which selectively reacts with carbon monoxide. In a less preferred embodiment the trapping is reversible so that the trapped carbon monoxide may be released for subsequent analysis by the mass spectrometer at a convenient time. In the case of a molecular sieve trap this can be achieved by heating.

The second preferred method, applicable when only nitrogen isotopes are to be determined, comprises converting the carbon monoxide present in the effluent of the catalytic reactor into a species whose mass spectrum does not contain peaks at masses 28 and 29, thereby enabling the nitrogen isotopic composition to be determined without interference. Preferably the carbon monoxide is converted into a species of lower molecular weight than carbon monoxide, for example methane. The conversion may be carried out by passing the effluent from the catalytic reactor through a methanizer containing a nickel catalyst at 400° C., thereby substantially completely converting the carbon monoxide into methane by reaction with hydrogen present in the effluent of the catalytic reactor. The reaction which takes place can be represented by $$CO + 3H_2 = CH_4 + H_2O$$

The hydrogen required for the conversion may be added to the gas flow between the exit of the catalytic reactor and the entrance of the methanizer. Alternatively, carrier gas comprising hydrogen, for example, a hydrogen/helium mixture, may be used. In certain cases, sufficient hydrogen may be available in the effluent of the catalytic reactor as a consequence of the decomposition of the sample, and additional hydrogen may not be necessary.

Preferably also a chromatographic "cutting" system is used to ensure that no other material enters the catalytic reactor while the effluent from the reactor analyzed.

Viewed from another aspect the invention provides apparatus for determining the isotopic composition of at least one element comprised in a sample, said apparatus comprising:
1) a catalytic reactor, said reactor containing elemental carbon and being arranged for the pyrolysis of samples introduced therein;
2) means for introducing a said sample into a flow of carrier gas;
3) first conduit means for conveying said carrier gas from said means for introducing said sample to said catalytic reactor whereby said sample is so pyrolyzed that:
    a) any carbon in said sample is converted into elemental carbon which is deposited in said reactor;
    b) any oxygen in said sample is substantially completely converted to carbon monoxide by reaction with elemental carbon in said reactor;
    c) any hydrogen in said sample is substantially completely converted to molecular hydrogen; and
    d) any nitrogen in said sample is substantially completely converted to molecular nitrogen;
4) a mass spectrometer for determining the isotopic composition of at least one element comprised in the group hydrogen, oxygen and nitrogen in the form of molecular hydrogen, carbon monoxide or molecular nitrogen, respectively; and
5) second conduit means for conveying effluent from said catalytic reactor to said mass spectrometer.

As previously explained, the requisite elemental carbon may be placed in the reactor prior to use. Alternatively, means may be provided for introducing a carbonaceous compound into the reactor in order to pyrolyze it to elemental carbon which is deposited in the reactor, as also previously explained.

The invention further provides apparatus for determining the isotopic composition of an element comprised in a carbonaceous sample, said apparatus comprising:
1) means for introducing a said sample into a flow of carrier gas;
2) a catalytic reactor, said reactor containing elemental carbon and being arranged to so pyrolyze a said sample that:
    a) the carbon in said sample is converted into elemental carbon which is deposited in said reactor;
    b) any oxygen present in said sample is substantially completely converted to carbon monoxide by reaction with elemental carbon in said reactor;
    c) any hydrogen present in said sample is substantially completely converted to molecular hydrogen; and
    d) any nitrogen present in said sample is substantially completely converted to molecular nitrogen;
3) first conduit means for conveying said carrier gas from said means for introducing said sample to said catalytic reactor;
4) a mass spectrometer arranged for the determination of the isotopic composition of at least one element selected from the group oxygen, nitrogen and hydrogen in the form of carbon monoxide, molecular nitrogen or molecular hydrogen respectively; and
5) second conduit means for conveying effluent from said catalytic reactor into said mass spectrometer.

The invention further comprises apparatus for determining the isotopic composition of carbon comprised in a sample, comprising:
1) a catalytic reactor, said reactor containing elemental carbon and being arranged for the pyrolysis of samples introduced therein;
2) means for introducing a said sample into a flow of carrier gas;
3) first conduit means for conveying said carrier gas from said means for introducing said sample to said catalytic reactor whereby said sample is so pyrolyzed that the carbon in said sample is converted into elemental carbon which is deposited in said reactor;
4) means, operable after pyrolysis of a said sample in said reactor, for introducing into said carrier gas an oxygenated compound, preferably water, to react with said elemental carbon in said reactor to produce carbon monoxide;
5) a mass spectrometer for determining the isotopic composition of said carbon monoxide; and
6) second conduit means for conveying effluent from said catalytic reactor to said mass spectrometer.

In a preferred embodiment, apparatus according to the invention further comprises a gas-chromatographic column disposed between the means for introducing the sample and the catalytic reactor, whereby the isotopic composition of at least some of the constituents of a mixture may be determined.

In a still further preferred embodiment, apparatus according to the invention further comprises means, disposed between the catalytic reactor and the mass spectrometer, for selectively absorbing at least carbon monoxide. Preferably the means for selectively absorbing comprises a chromatographic column capable of temporally separating nitrogen and carbon monoxide, for example a "Poraplot Q" or molecular sieve column maintained at −4° C.

Alternatively, the means for selectively absorbing may comprise a trap capable of removing carbon monoxide from the reactor effluent. Such a trap may comprise a cooled molecular sieve or a material which selectively reacts with carbon monoxide.

In a less preferred embodiment the trap, for example a molecular sieve, reversibly absorbs carbon monoxide. Means, for example a heater, are also provided for expelling the carbon monoxide from the trap to allow its analysis at any convenient time.

In another preferred embodiment, applicable when nitrogen isotopes only are to be determined, means may be provided downstream of the catalytic reactor for converting any carbon monoxide formed in the reactor to a species whose mass spectrum does not contain peaks at masses 28 and 29, for example methane. To this end a methanizer comprising a nickel catalyst maintained at 400° C. by an electrical heater may be provided between the catalytic reactor and the mass spectrometer. The hydrogen required for the methanization may be introduced through a tee connection between the catalytic reactor and the methanizer, or alternatively a carrier gas comprising hydrogen can be used. In certain cases the decomposition of an hydrogenous sample in the catalytic reactor may provide sufficient hydrogen for the methanization so that no additional hydrogen is needed.

The catalytic reactor may comprise a tube which contains the carbon required for the above-described chemical processes which take place in the reactor. Such a reactor, wherein the tube containing the carbon is maintained at 1000° C., is discussed by Kaiser and Rieder, Proc. Fourth Int Clean Air Congress, Tokyo, 1977, pp 451–4, the referenced article discussing use of such a reactor in an oxygen-specific flame-ionization detector. The manner of introduction of the carbon into the reactor tube is a matter of choice, i.e., the introduction may either be prior to operation or result from the pyrolysis of a carbonaceous sample. When hydrogen is not to be determined, the catalytic reactor may comprise a 90% platinum/10% rhodium alloy capillary tube approximately 0.5 mm internal diameter and 0.5 m long. This may be heated to approximately 1200°–1500° C. by passing an electrical current through it. The capacity of such a catalytic reactor is dependent on temperature, being significantly greater at higher temperatures, but this increased capacity is obtained only at the expense of reactor lifetime. For most purposes, a temperature of 1200° C. represents the best compromise between dynamic range and lifetime. The behaviour of a reactor of this type has been discussed in detail by Steinmüller (ibid). Steinmüller also discusses the presence of certain side reactions in the catalytic reactor and shows that at 1200° C. the effect of these is insignificant for the purposes of an OSD. Similarly, the present inventors have confirmed that side reactions do not significantly detract from the accuracy of the present method.

BRIEF DESCRIPTION OF DRAWINGS

Preferred embodiments of the invention will now be described in greater detail by way of example only and with reference to the accompanying drawings, in which.

Figure 1:
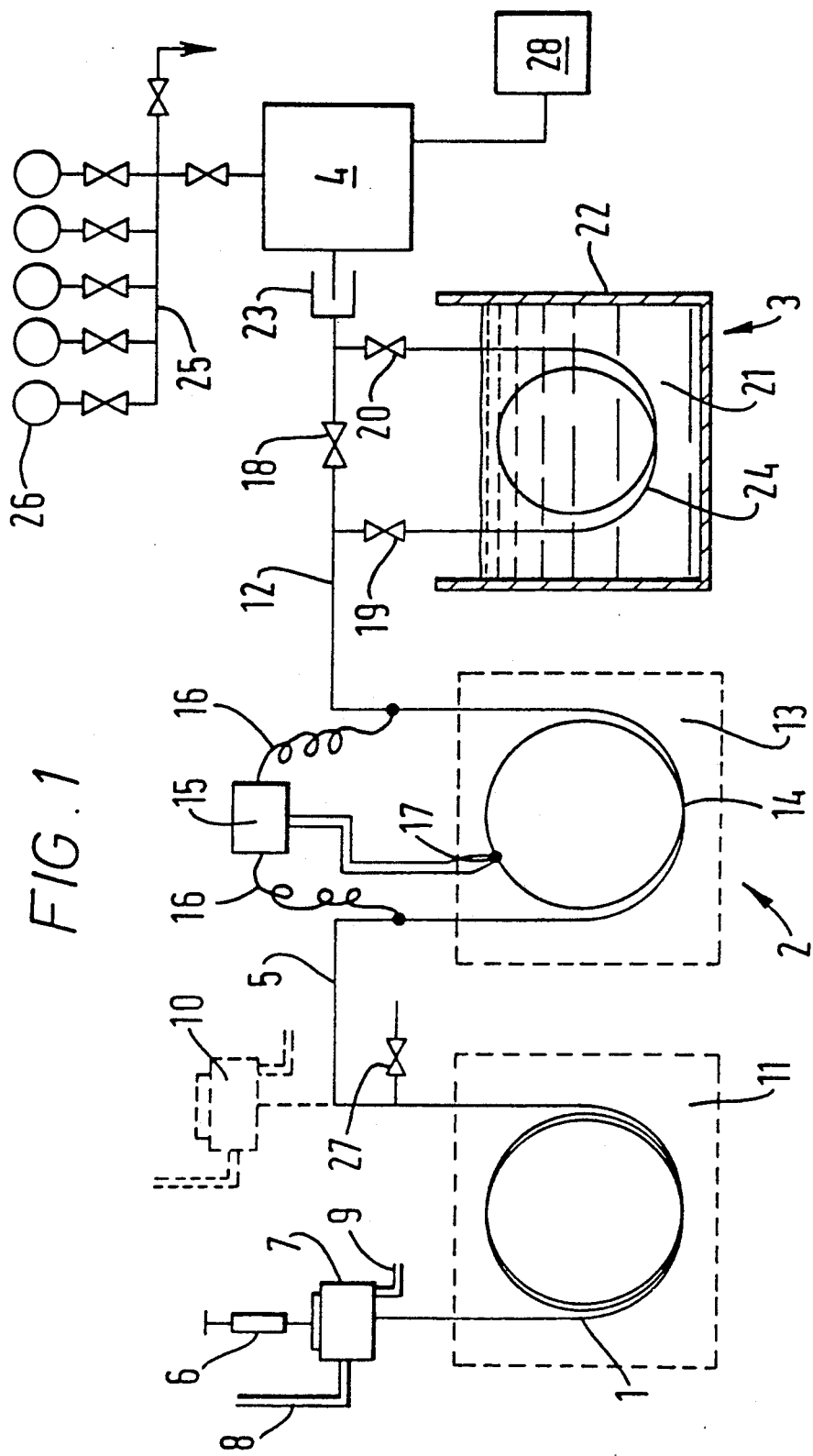
FIG. 1 is a schematic drawing of a preferred embodiment of the apparatus of the invention.

Referring first to FIG. 1, apparatus for carrying out the method of the invention comprises a gas-chromatographic column 1 disposed in a conventional temperature-controlled oven 11, a heated catalytic reactor 2, means 3 for selectively absorbing at least carbon monoxide, and a mass spectrometer 4. First conduit means 5 connect the column 1 to the reactor 2, and second conduit means 12 connect the reactor 2 to the means 3 and mass spectrometer 4. Both conduit means 5 and 12 comprise stainless steel or quartz capillary tubing. An open splitter 23 is disposed in the inlet to the mass spectrometer 4 to ensure a constant flow.

A conventional injector 7 is provided to introduce a sample contained in syringe 6 into a flow of a carrier gas introduced into the inlet 8. A vent 9 on the injector 7 discharges excess carrier gas and sample in the preferred case where column 1 is a capillary column. The carrier gas employed is conveniently helium, but other inert gases can be used, providing that they do not contain any of the elements whose isotopic composition is to be determined.

In cases where the samples to be analyzed are pure compounds or are such that no prior GC separation is required, the column 1 can be omitted and the injector located at the alternative position 10, enabling the samples to be introduced directly into the catalytic reactor.

The catalytic reactor 2 comprises, in the preferred embodiment, a tube 14 which contains the carbon required for the above described chemical processes which take place in the reactor. Tube 14 is disposed in an electric furnace 13 which is heated by passage of an electrical current from a power supply/controller 15 via the connecting leads 16. The current passed is sufficient to maintain the temperature of the tube at the preferred temperature of 1000° C. A thermocouple 17 is attached to the exterior of the reactor tube 14 and is connected to the temperature sensor input of the power supply/controller 15.

The effluent of the catalytic reactor tube 14, flowing in the second conduit means 12, can be admitted directly into the mass spectrometer 4 via the valve 18, or diverted through the means 3 for selectively absorbing at least carbon monoxide via valves 19 and 20. In cases where the sample does not contain both oxygen and nitrogen, the effluent from the reactor can be admitted directly into the spectrometer, but in other cases, the carbon monoxide produced in the catalytic reactor should be absorbed so that the nitrogen and carbon monoxide can be analyzed in the mass spectrometer without interference.

The means 3 for selectively absorbing at least carbon monoxide comprises a chromatographic capillary column 24, 0.3 mm inside diameter and 10 m long, packed with "Poraplot Q". The column is immersed in a bath 22 of coolant 21 which maintains it at a temperature of about −4° C. The retention time of carbon monoxide on such a column is longer than that of nitrogen so that nitrogen enters the mass spectrometer 4 and can be analyzed before the carbon monoxide has passed through the column.

The mass spectrometer 4 is a dual-inlet, triple collector type which is capable of analyzing both major and minor isotope ion beams simultaneously. It is adapted to analyze gaseous samples of carbon monoxide, nitrogen, and/or hydrogen, as required. One inlet is used for the input of the converted sample from the second conduit means 12 and/or the means 3 for selectively absorbing at least carbon monoxide, and the other is connected to a manifold 25 to which a number of reservoirs, for example 26, can be attached. One of the reservoirs 26 is charged with a suitable reference gas for each of the analyses to be carried out, e.g., a sample of carbon monoxide of accurately known isotopic composition is used as the reference gas for the determination of the oxygen isotopic composition of the sample. Mass spectrometer 4 and the valves associated with the inlet system are automatically operated by a suitably programmed computer 28, as is conventional. Computer 28 is also used to store and to process the output of the spectrometer.

According to the invention elemental carbon should be present inside the tube 14. It is not essential that the carbon be placed in the reactor tube 14 on assembly. Rather, carbon may be deposited in the tube by the pyrolysis of a carbonaceous compound. In some cases the pyrolysis of the sample itself will provide enough carbon, but, except when carbon is to be determined, in view of the dependence of the process on the presence of excess carbon it is desirable to use the additional inlet 27 to admit a carbonaceous gas (conveniently a hydrocarbon gas such as propane) into the capillary reactor 14 for several minutes prior to the injection of the sample from the syringe 6. This will ensure the presence of sufficient carbon for at least one analysis of a sample mixture at the loading appropriate for a capillary GC column, and usually for several such analyses.

A preferred method of operation of the apparatus is as follows:

First, propane is admitted via valve 27 as described above. Valve 27 is then closed and the carrier gas (helium) is introduced into inlet 8 until all traces of the propane have been swept from the system. The mass spectrometer is adjusted to monitor the m/e values of the isotopes to be determined and the helium flow continued until the outputs are stable. A sample of the reference gas is then analyzed and the sample (typically a mixture of organic compounds) injected into the injector 7 from syringe 6. The GC column 1 temporally separates the various components of the mixture so that they pass in sequence into the catalytic reactor 2 where they are converted into carbon monoxide, hydrogen and nitrogen.

When a particular component in the sample comprises both nitrogen and oxygen, the effluent from the GC column is conveyed into the capillary column 24 via the second conduit means 12 and valve 19. As explained, this is maintained at $-4°$ C. or lower by the coolant in the bath 22. Alternatively, if the particular component does not contain both nitrogen and oxygen, the effluent from the catalytic converter can be routed via valve 18 directly into the mass spectrometer 4.

Mass spectrometer 4 is adjusted to simultaneously monitor the ion currents due to the major and minor isotopes of the element to be determined, for example, masses 2 and 3 for the determination of hydrogen, masses 28, 29 and 30 for the determination of oxygen in the form of carbon monoxide. Reference samples of gas of accurately known isotopic composition from the reservoirs 26 are also analyzed by mass spectrometer 4, preferably just prior and just after the period in which the constituent of interest is entering the spectrometer. The isotopic composition of an element in that component is then determined relative to that of the reference gas in a conventional way. The whole mass spectrometric process is controlled by the digital computer 28, which operates in a conventional manner.

Figure 2:
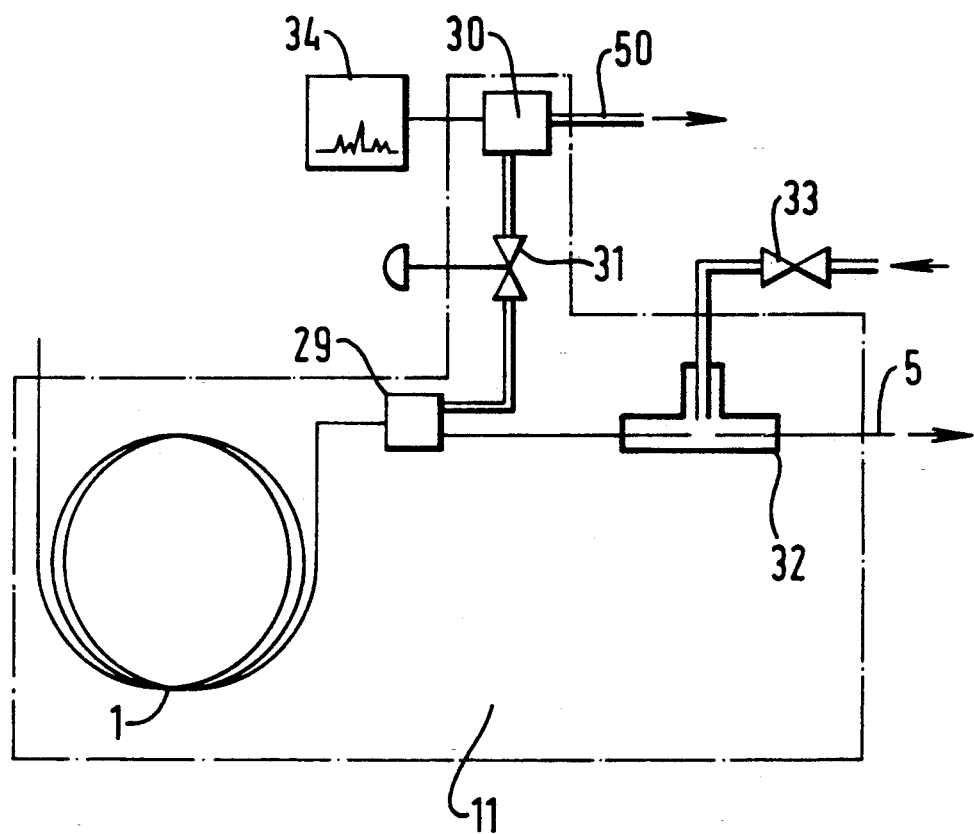
FIG. 2 is a schematic drawing of part of an apparatus according to the invention incorporating certain additional features.

There is a risk that, because of the delay in the carbon monoxide analysis occasioned by the column 24, in the case of a complex mixture it will not be possible to analyze the carbon monoxide before nitrogen from another constituent enters the mass spectrometer. In this situation it is advisable to use a heart-cutting technique to ensure that only the component to be analyzed is converted in the catalytic reactor. Suitable apparatus for carrying out this technique is shown in FIG. 2. Instead of connecting directly to the catalytic reactor tube 14, the outlet of the column 1 is connected to a splitter 29 located in the chromatograph oven 11. Splitter 29 divides the effluent from the column into two portions, one leading to a gas chromatographic detector 30 (typically a flame ionization detector) via a control valve 31 and the other leading to a make-up tee 32. The detector 30 vents to atmospheric pressure so that the impedance of the path from the splitter 29 is much lower than that leading to the make-up tee 32. Consequently, when the valve 31 is fully open, substantially all the effluent from the column 1 is directed through the detector 30 and vent 50 and does not enter the catalytic reactor 2. In this situation, an additional supply of carrier gas is admitted into the make-up tee 32 via valve 33, maintaining approximately constant the flow of carrier gas through the catalytic reactor 2 and the means 3 for selectively absorbing at least carbon dioxide. In this way the elution of carbon monoxide absorbed in the column 24 may continue without interruption, permitting the analysis by mass spectrometer 4.

In use, valve 31 is closed only to allow the effluent from column 1 to pass into the catalytic reactor 2 when a component of interest is eluting. When valve 31 is open, the detector 30, connected to an amplifier and a recorder 34, can be used to monitor the progress of the chromatography. If the times at which the components to be analyzed are sufficiently well known, the detector 30 and recorder 34 can of course be omitted, and the outlet of the control valve 31 vented to atmospheric pressure.

Figure 3:
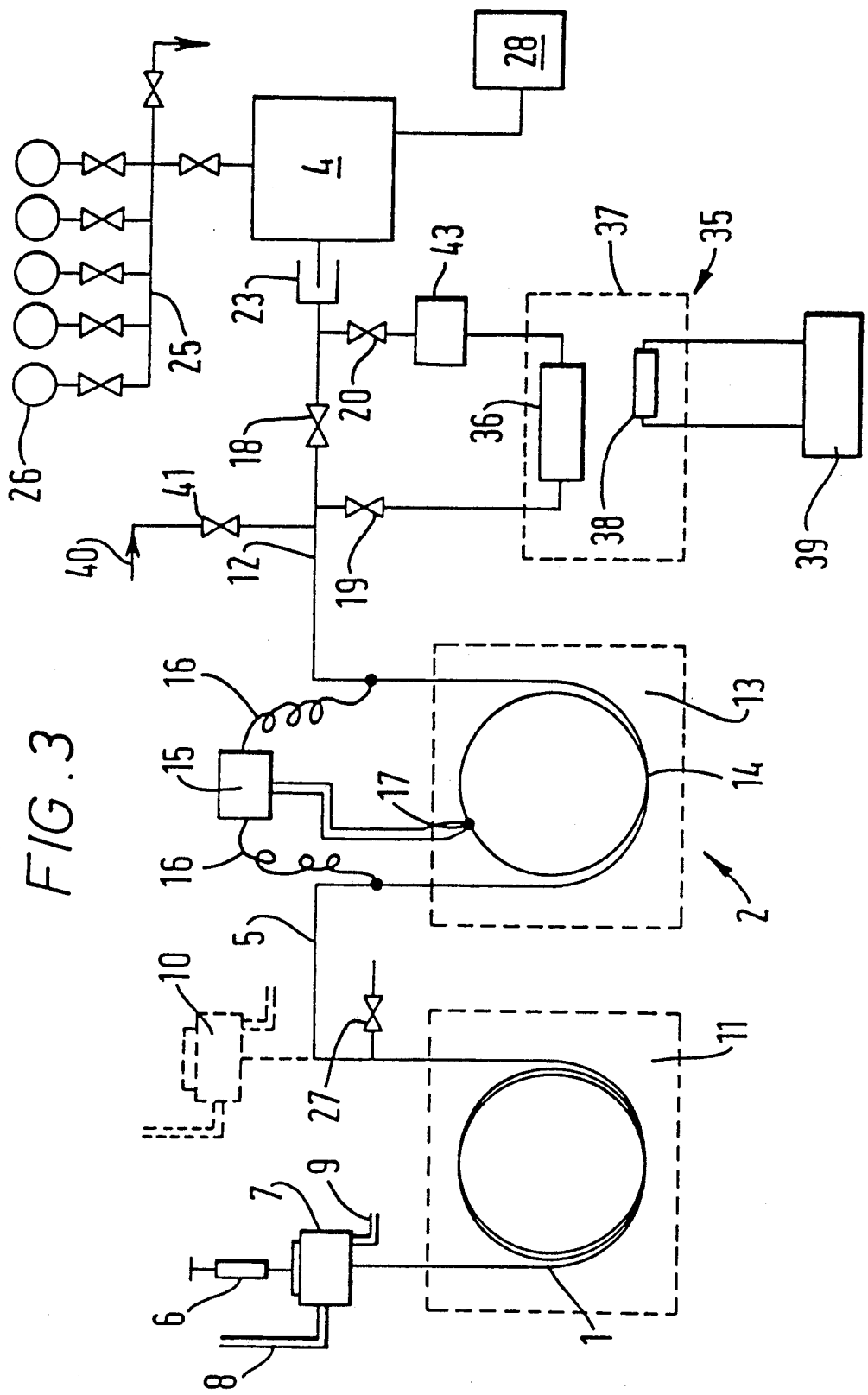
FIG. 3 is a schematic drawing of a preferred embodiment of the apparatus of the invention suitable for the determination of nitrogen isotopes only.

When only nitrogen isotopes are to be determined the apparatus shown in FIG. 3 may be employed. This differs from the previous embodiments in that the means 3 for selectively absorbing at least carbon monoxide is replaced by a methanizer 35 which comprises a tube 36 packed with nickel connected between valves 19 and 20. Tube 36 is enclosed in an oven 37 which maintains the tube 36 at a temperature of about 400° C. by means of an electrical heater 38 powered from a power supply/controller 39. Hydrogen gas is introduced into the methanizer 36 through inlet pipe 40 and control valve 41 to ensure that all the carbon monoxide in the effluent from the catalytic reactor 2 is converted to methane. The flow of gas through the open splitter 23 into the mass spectrometer 4 comprises therefore only hydrogen, nitrogen, methane and water, so that the isotopic composition of the nitrogen can be determined at relatively low resolution.

Advantage may also be had by including a trap 43 in the exit of the methanizer 36 to remove water generated by the methanization reaction, thereby preventing contamination of the mass spectrometer 4 and the associated inlet pipework. Trap 43 may conveniently comprise a coiled capillary tube maintained at approximately $-100°$ C., for example by means of liquid nitrogen or another suitable coolant.

We claim:

1. A method of determining the isotopic composition of carbon comprised in a sample, said method comprising the steps of:
   i) introducing said sample into a flow of non-carbonaceous carrier gas and conveying said carrier gas to a catalytic reactor, said reactor containing elemental carbon, wherein said sample is pyrolyzed to deposit elemental carbon in said reactor;
   ii) introducing into said catalytic reactor a non-carbonaceous oxygenated compound which reacts with said elemental carbon to produce carbon monoxide;
   iii) conveying at least some of the gases emerging from said catalytic reactor into a mass spectrometer;
   iv) determining the isotopic composition of the carbon comprised in said sample by said spectrometric measurements made on said carbon monoxide.

2. A method for the isotopic analysis of nitrogen in a sample comprising the sequential operation of the following steps:
   i) causing a carrier gas which does not comprise any nitrogen to flow through a heated catalytic reactor;
   ii) introducing said sample into said flow of carrier gas before it enters said catalytic reactor so that said sample is pyrolized in said reactor and
      a) any carbon present in said sample is converted to elemental carbon which is deposited in said reactor,
      b) any oxygen present in said sample is substantially completely converted to carbon monoxide by reaction with elemental carbon in said reactor,
      c) any hydrogen present in said sample is substantially completely converted to molecular hydrogen, and
      d) any nitrogen present in said sample is substantially completely converted to molecular nitrogen;
   iii) passing effluent from said catalytic reactor through a methanizer to reduce said carbon monoxide to methane;
   iv) conveying at least some of the gases emerging from said methanizer into a mass spectrometer; and
   v) determining the isotopic composition of the nitrogen by mass spectrometric measurements made on said molecular nitrogen.

3. A method for the isotopic analysis of nitrogen and/or oxygen in a sample comprising the sequential operation of the following steps:
   i) causing a carrier gas which does not comprise any nitrogen and/or oxygen to flow through a heated catalytic reactor, said reactor containing carbon maintained at about 1000° C.;
   ii) introducing said sample into said flow of carrier gas before it enters said catalytic reactor so that said sample is pyrolized in said reactor and
      a) any carbon present in said sample is converted to elemental carbon which is deposited in said reactor,
      b) any oxygen present in said sample is substantially completely converted to carbon monoxide by reaction with elemental carbon in said reactor,
      c) any hydrogen present in said sample is substantially completely converted to molecular hydrogen, and
      d) any nitrogen present in said sample is substantially completely converted to molecular nitrogen;
   iii) passing at least some of the effluent from said catalytic reactor through a chromatographic column to temporally separate carbon monoxide and nitrogen;
   iv) conveying at least some of the gases emerging from said chromatopgraphic column into a mass spectrometer; and
   v) determining the isotopic composition of at least one said element selected from the group consisting of nitrogen and oxygen by mass spectrometric measurements made on said carbon monoxide or molecular nitrogen.

4. A method of determining the isotopic composition of at least one element of a sample, the said element being selected from carbon, nitrogen and oxygen, said method comprising the sequential operation of the following steps:
   i) causing a carrier gas which does not comprise any or said selected element to flow through a heated catalytic reactor, said reactor containing carbon and comprising a platinum/rhodium alloy catalyst maintained at about 1200° C.;
   ii) introducing said sample into said flow of carrier gas before it enters said catalytic reactor so that said sample is pyrolyzed in said reactor and
      a) any carbon present in said sample is converted to elemental carbon which is deposited in said reactor,
      b) any oxygen present in said sample is substantially completely converted to carbon monoxide by reaction with elemental carbon in said reactor,
      c) any hydrogen present in said sample is substantially completely converted to molecular hydrogen, and
      d) any nitrogen present in said sample is substantially completely converted to molecular nitrogen;
   iii) conveying at least some of the gases emerging from said catalytic reactor into a mass spectrometer; and
   iv) determining the isotopic composition of at least one said element selected from the group consisting of oxygen, nitrogen and hydrogen by mass spectrometric measurements made on said carbon monoxide, molecular nitrogen or molecular hydrogen respectively.

5. A method of determining the isotopic composition of at least one element of a sample, the said element being selected from carbon, nitrogen and oxygen, said method comprising the sequential operation of the following steps:
   i) causing a carrier gas which does not comprise any of said selected element to flow through a heated catalytic reactor, said reactor containing carbon maintained at about 1000° C.;
   ii) introducing said sample into said flow of carrier gas before it enters said catalytic reactor so that said sample is pyrolyzed in said reactor and
      a) any carbon present in said sample is converted to elemental carbon which is deposited in said reactor,
      b) any oxygen present in said sample is substantially completely converted to carbon monoxide by reaction with elemental carbon in said reactor, c) any hydrogen present in said sample is substantially completely converted to molecular hydrogen, and d) any nitrogen present in said sample is substantially completely converted to molecular nitrogen;

iii) conveying at least some of the gases emerging from said catalytic reactor into a mass spectrometer; and iv) determining the isotopic composition of at least one said element selected from the group consisting of oxygen, nitrogen and hydrogen by mass spectrometric measurements made on said carbon monoxide, molecular nitrogen or molecular hydrogen respectively.

6. A method as claimed in claim 5 wherein prior to the admission of said sample elemental carbon is deposited in said catalytic reactor by the pyrolysis therein of a carbonaceous material.

7. A method as claimed in claim 5 wherein said sample comprises a carbonaceous sample and elemental carbon is deposited in said reactor by the pyrolysis of said carbonaceous sample.

8. A method as claimed in claim 5 wherein said sample comprises a mixture of constituent materials and wherein said method further comprises passing said carrier gas through a chromatographic column to temporally separate at least some of said constituent materials prior to their entering said catalytic reactor.

9. A method as claimed in claim 5 for the isotopic analysis of nitrogen and/or oxygen comprised in a sample, said method further comprising the step of passing effluent of said catalytic reactor prior to its admission into said mass spectrometer through a chromatographic column to temporally separate said carbon monoxide and said nitrogen.

* * * * *